United States Patent [19]
Fahnestock

[11] Patent Number: 4,617,266
[45] Date of Patent: Oct. 14, 1986

[54] PRODUCTION OF PROTEIN A

[75] Inventor: Stephen R. Fahnestock, Brookeville, Md.

[73] Assignee: Genex Corporation, Gaithersburg, Md.

[21] Appl. No.: 489,326

[22] Filed: Apr. 28, 1983

[51] Int. Cl.[4] .................. C12P 21/00; C12N 15/00; C12N 1/20; C12N 1/00
[52] U.S. Cl. .................................. 435/68; 435/172.3; 435/253; 435/317; 435/70; 935/6; 935/11; 935/29; 935/38
[58] Field of Search .................................. 435/68–71, 435/172, 253, 317, 172.3; 935/6, 11, 29, 38

[56] References Cited
PUBLICATIONS

Kreft et al, Current Topics in Microbiology and Immunity vol. 96, pp. 1–17, (1982).
Young, Journal of General Microbiology, vol. 119, pp. 1–15 (1980).
Sven Lofdahl, et al., Gene for Staphylococcal Protein A, 10/26/82, pp. 697–701, PNAS, vol. 80.
Arne Forsgren, Significance of Protein A Production by Staphylococci, 08/04/70, pp. 672–673, Infection and Immunity, vol. 2.
John Sjoquist, et al., Localization of Protein A in the Bacteria, 05/23/72, pp. 190–194, Eur. J. Biochem, vol. 30.
Roger Lindmark, et al., Extracellular Protein A from Methicillin-Resistant Strain of *Staphylococcus aureus*, 10/26/76, pp. 623–628, Euro. J. Biochem, vol. 30.

Primary Examiner—Alvin E. Tanenholtz
Attorney, Agent, or Firm—Bernard, Rothwell & Brown

[57] ABSTRACT

Novel Protein A-producing Gram-positive bacterial strains and methods for their preparation are disclosed. Also disclosed are methods for producing Protein A using the novel Gram-positive strains.

12 Claims, 2 Drawing Figures

PRODUCTION OF PROTEIN A

BACKGROUND OF THE INVENTION

Protein A is a cell wall component produced by nearly all strains of Staphylococcus aureus (see e.g. Forsgren, A., Infection and Immunity 2: 672-673 [1970]); and Sjoquist, J. et al., Eur. J. Biochem. 30: 190-194 [1972]). Protein A is useful in that it binds strongly and specifically to the Fc portion of immunoglobulin IgG from a variety of mammalian sources, including human (Kronvall, G. et al., J. Immunol. 103: 828-833 [1969]). Thus this protein has been used in diagnostic applications and has potential therapeutic value.

In most S. aureus strains, at least 70% of the Protein A produced is covalently linked to the peptidoglycan of the cell wall (Sjoquist, J. et al., Eur. J. Biochem. 30: 190-194 [1972]. The site of attachment is the C-terminal region of the Protein A molecule (Sjodahl, J., Eur. J. Biochem. 73: 343-351 [1977]). Some Protein A (15-30%) is generally excreted into the growth medium, and there are several circumstances under which the fraction of Protein A which is excreted can be increased. Some methicillin resistant strains of S. aureus excrete essentially all their Protein A (Lindmark, R. et al., Eur. J. Biochem. 74: 623-628 [1977]). Low levels of puromycin increase the amount of excreted Protein A, presumably by truncating the protein and thereby eliminating its C-terminal cell wall attachment site, and protoplasts excrete nearly all the Protein A which they synthesize (Movitz, J., Eur. J. Biochem. 68: 291-299 [1976]).

Protein sequence information is available for Protein A from S. aureus strain Cowan I (Sjodahl, J., Eur. J. Biochem. 78: 471-490 [1977]). The Cowan I strain contains approximately $2 \times 10^5$ molecules of Protein A per cell (Sjoquist, J. et al., Eur. J. Biochem. 30: 190-194 [1972]).

Protein A is synthesized in S. aureus only during exponential growth, and synthesis ceases as the culture approaches stationary phase (Movitz, J., Eur. J. Biochem. 48: 131-136 [1974]). The level of synthesis of Protein A in S. aureus is highly variable, and is strongly influenced by the growth conditions in some as yet poorly defined ways (Landwall, P., J. Applied Bact. 44: 151-158 [1978]).

The Protein A gene from S. aureus strain Cowan I has been cloned in E. coli. Lofdahl, S., et al., Proc. Natl. Acad. Sci. USA, 80, 697-701 (1983). This gene is contained in a 2.15 kilobase insert bounded by EcoRV restriction sites. The gene has been inserted into a plasmid and cloned in E. coli, where low levels of expression have been achieved. The chimeric plasmid which contains the Protein A gene has been designated "pSPA1."

Currently, industrial production of Protein A is carried out using mutant strains of S. aureus. A major disadvantage of using S. aureus to produce Protein A is that all available production strains are human pathogens. Although many genetic engineering experiments have been conducted using Escherichia coli, that organism is not suitable for efficient production of Protein A, since it does not export protein outside the cell. Furthermore, E. coli possesses disadvantageous pathogenic properties as well, i.e., produces endotoxins.

There thus remains a need for the production of Protein A by means which are both safe and efficient.

SUMMARY OF THE INVENTION

In accordance with the present invention, Protein A-producing Gram-positive bacteria are prepared by introduction into Gram-positive cells which do not normally produce Protein A, vectors containing the nucleotide sequence coding for Protein A and expression signals directing expression of the Protein A gene in the microorganism. Protein A can be produced by cultivating such cells in a nutrient medium under protein-producing conditions.

DETAILED DESCRIPTION OF THE INVENTION

Figure 1:
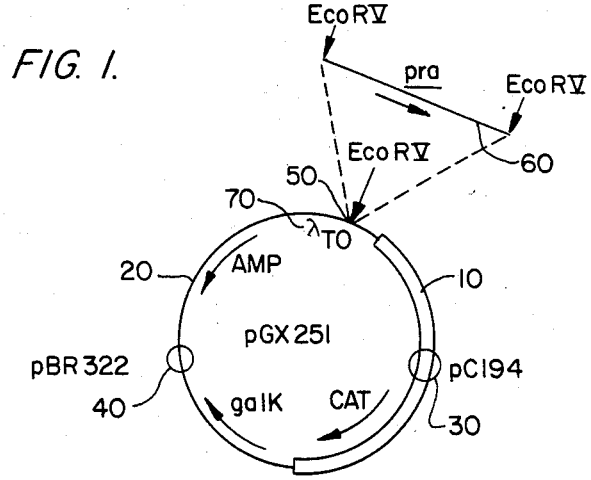

A method of achieving high level production of Protein A in Gram-positive microorganisms without substantially inhibiting the growth of the host has been discovered. The method involves transformation of a Gram-positive microorganism by introduction therein of a vector containing the nucleotide sequence coding for Protein A. A Protein A gene may be obtained from Protein A-producing microorganisms, such as the above-mentioned strains of S. aureus. A preferred source of the gene is plasmid pSPA1, which has been cloned in E. coli. See Lofdahl, S., et al. (supra). The gene may advantageously be excised from that clone by digestion with endonuclease EcoRV.

The Protein A gene may contain its natural expression signals (i.e., transcriptional and translational initiation sequences), or those signals may be replaced by other expression signals recognizable by the Gram-positive host microorganism. Replacement of the natural expression signals with other recognizable Gram-positive expression signals may be accomplished using conventional methods of molecular biology. Such replacement involves cleavage of the natural expression signals from the Protein A sequence and fusion of the desired expression signals to the Protein A gene.

Construction of the Protein A-producing strains of this invention involves inserting, by recombinant DNA techniques, the Protein A gene into a plasmid vector. Such a vector may be prepared in vitro and inserted directly into the Gram-positive bacterial host by transformation techniques. The vector is preferably cloned in another organism for amplification and purification prior to transformation of the ultimate Gram-positive host cells. The microorganism used for the intermediate cloning step may be an organism in which the vector will be maintained and express selectable phenotypical properties. E. coli is the preferred microorganism for the intermediate cloning step.

When the vector is constructed in vitro and first cloned in E. coli, it advantageously contains a functional E. coli replicon as well as a phenotypic marker for E. coli. The vector also advantageously contains a phenotypic marker for the Gram-positive host microorganism. In one embodiment of the present invention, the vector also contains a functional replicon permitting autonomous replication in the Gram-positive bacteria selected. One or more copies of the Protein A gene may be inserted into this vector, and the vector then used to transform the appropriate Gram-positive microorganism.

In preferred embodiments of this invention, the vector does not contain a replicon capable of functioning in the Gram-positive microorganism selected, but rather contains a DNA sequence homologous to a region of the chromosome of that Gram-positive microorganism. This construction permits linear integration of the vector into the host chromosome in the region of homology. The vector is again advantageously constructed in vitro and first cloned in *E. coli* as above; however, if desired, the gram-positive bacterial host may be transformed directly with the chimeric plasmid. Such a vector transforms the Gram-positive microorganism by recombination with the homologous region of Gram-positive host chromosome. An advantage of this method is that there is less likelihood of loss of the Protein A sequence from the host, due to negative selection favoring plasmid-free cells, and Protein-A producing strains prepared in this manner have been found to be genetically stable.

The Gram-positive host microorganisms employed in this invention are advantageously selected from non-pathogenic strains which do not normally synthesize Protein A. Although the invention will be described in detail with regard to *Bacillus subtilis*, it is to be understood and will be appreciated by those skilled in the art that the invention is applicable to a variety of Gram-positive microorganisms. Particularly preferred host microorganisms are well known industrial strains of the genera, Bacillus and Streptomyces. Generally, it has been found that Protein A is produced at optimum levels during the exponential growth phase of the organisms, and production slows considerably thereafter. It has also been found that the period of Protein A synthesis can be extended using sporulation deficient (spo−) Gram-positive hosts. When spo− hosts are used, the resulting strains are generally genetically more stable, the level of Protein A is higher, and, because fewer proteases are produced by these cells, the Protein A product is more stable.

Transformation of the Gram-positive microorganism may be accomplished by any suitable means. A particularly preferred transformation technique for these organisms is to remove the cell wall by lysozyme digestion, followed by transformation of the resulting protoplasts. Chang, S., et al. *Molec. Gen. Genet.*, 168, 111–115 (1979). Alternatively, cells competent for transformation can be transformed by a modification of the method of Anagnostopoulos, C., et al., *J. Bacteriol.*, 81, 741–746 (1961), as described in Example III below.

The procedures used to clone the Protein A gene and construct Protein A-producing strains of *B. subtilis* described herein are, except where otherwise indicated, accomplished by using conventional techniques of molecular biology. Segments of DNA containing the sequence coding for Protein A are isolated. If the sequences contain the natural expression signals for Protein A, the segments may be inserted into an appropriate vector without further modification. If the sequences do not contain the natural expression signals, or it is desired to replace them, the existing expression signals (if present) may be enzymatically removed and a DNA sequence containing the desired expression signals may then be fused to the Protein A gene. The Protein A sequences attached to the desired expression signals may then be inserted into an appropriate vector.

Vectors appropriate for transformation of *B. subtilis* are generally plasmids, and are advantageously constructed in *E. coli*. Such vectors contain a functional *E. coli* replicon, a phenotypic marker for *E. coli*, and a phenotypic marker for *B. subtilis*. The vector may also contain a *B. subtilis* replicon, but preferably it does not and instead contains a DNA sequence homologous to a region of the *B. subtilis* chromosome. Insertion of the homologous DNA sequence into the vector permits recombination of the vector with the *B. subtilis* chromosome, where it can be maintained at a copy number of one per genomic equivalent.

One or more copies of the DNA sequences coding for Protein A and the desired expression signals are then inserted into the vector. The presence of the *E. coli* replicon and phenotypic marker in the vector permit its cloning and maintenance in *E. coli*, and allow for selection of clones containing the vector.

When an intermediate cloning step in *E. coli* is employed, one or more *E. coli* colonies which carry the Protein A-containing plasmid are grown on suitable nutrient media, and the plasmids are isolated therefrom. Cells of *B. subtilis* (i.e. competent cells of protoplasts) are then transformed by introduction therein of the vector and successful transformants are selected by means of the *B. subtilis* phenotypic marker. Vectors containing a *B. subtilis* replicon are capable of reproducing in the host and producing Protein A when the cells are grown under protein-producing conditions. Alternatively, vectors not containing a *B. subtilis* replicon but instead containing a DNA sequence homologous with the host chromosome will recombine with the host chromosome and be replicated along with the host chromosome.

Preferred plasmid vectors for the cloning procedures described herein are graphically illustrated in the drawings.

FIG. 1 depicts a vector designated pGX251, which was constructed from the *E. coli* vector pBR322 and the *B. subtilis* vector pC194. In FIG. 1, the pC194 sequence 10 containing *B. subtilis* replicon 30 is fused to pBR322 sequence 20 containing *E. coli* replicon 40. The pC194 sequence contains the CAT gene, which specifies resistance to chloramphenicol. The pBR322 sequence contains a galactokinase (galK) gene, a gene specifying ampicillin resistance (amp) and a transcription termination sequence 70 derived from bacteriophage lambda. Plasmid pGX251 contains a unique EcoRV restriction site which provides a convenient insertion site for the EcoRV fragment 60 from pSPA1 which contains the protein A gene (pra). The most prevalent orientation of the pra gene is illustrated, but either orientation can be employed, since the pSPA1 EcoRV segment contains the appropriate expression signals.

Figure 2:
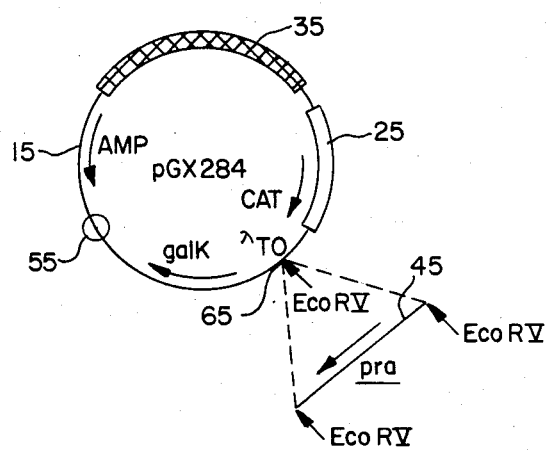

FIG. 2 depicts plasmid pGX284, which is the preferred vector for the practice of the present invention. In FIG. 2, pBR322 sequence 15, containing *E. coli* replicon 55 was fused to pC194 sequence 25 containing no replicon. Like vector pGX251, pGX284 specifies ampicillin (amp) and chloramphenicol (CAT) resistance, contains the galactokinase (galK) gene, contains the lambda transcription termination sequence and the unique EcoRV recognition sequence 65, providing an insertion site for the Protein A gene-containing segment 45. In addition, pGX284 contains a segment of *B. subtilis* chromosomal sequences 35. The presence of these sequences and the absence of a *B. subtilis* replicon permits linear integration of this vector into the chromosomes of *B. subtilis* transformants.

A further embodiment of the present invention involves preparation of vectors differing in their homologous chromosomal DNA sequences, but still containing one or more copies of the Protein A gene. Thus, vectors can contain sequences from different regions of the *B.* subtilis chromosome, or even from chromosomes of different species of Bacillus. This permits integration of the vectors into different parts of the host chromosome in the corresponding regions of homology resulting in transformants with more than one vector incorporated in the host chromosome.

Transformed B. subtilis cells are grown in a nutrient medium under protein-producing conditions resulting in the production of Protein A by the cells and the secretion of Protein A into the medium. Protein A may then be purified from the medium after removing intact cells using conventional techniques.

Those skilled in the art will recognize that, although the present disclosure describes cloning and expression of the entire Protein A gene, functional segments of that gene or fusions of the gene with other DNA segments can also be cloned and expressed in accordance with the teachings herein. Such segments and fusions are, therefore, intended to be within the scope of this invention.

The invention is further illustrated by the following examples which are not intended to be limiting. For the DNA manipulation described in this and the following examples, the restriction endonucleases and other enzymes used were purchased from New England Biolabs, Inc., Bethesda Research Laboratories, Inc., Boehringer Mannheim GmbH, and were used in the conventional manner as recommended by the manufacturer, except as noted otherwise.

EXAMPLE I

Isolation of a DNA sequence containing the Protein A gene and Promoter Region

Plasmid pSPAI (consisting of a 7.6 kilobase pair insert of DNA derived from S. aureus strain 8325-4 in E. coli vector pBR322) at a concentration of 110 μg/ml was digested with restriction endonuclease EcoRV at 256 units/ml in a buffer ("EcoRV buffer") containing 150 mM NaCl, 6 mM Tris-HCl (pH 7.9), 6 mM $MgCl_2$, 6 mM 2-mercaptoethanol for 1 hour at 37° C., then for an additional 30 min. with an additional 256 units/ml EcoRV endonuclease. A small EcoRV fragment (2.15 kb) was isolated by agarose gel electrophoresis and electroelution, and found to obtain the Protein A gene and promoter region (see Examples II and IV).

EXAMPLE II

Insertion of the 2.15 kb pair fragment into Plasmid pGX251

Plasmid pGX251 (containing an E. coli replicon derived from plasmid pBR322, a B. subtilis replicon derived from plasmid pC194, the gene for ampicillin resistance, the gene for chloramphenicol resistance and a unique EcoRV site) was linearized by restriction endonuclease digestion with EcoRV (640 units/ml) at a concentration of 40 μg/ml in EcoRV buffer for 1 hour at 37° C. Digestion was terminated by incubation for 8 minutes at 65° C. and was determined to be complete by agarose gel electrophoresis. The 2.15 kb EcoRV fragment from Example I and linearized pGX251 were ligated at a concentration of 200 μg/ml EcoRV fragment, 100 μg/ml linearized pGX251, in a buffer ("ligation buffer") containing 50 mM Tris-HCl (pH 7.8), 10 mM $MgCl_2$, 2 mM dithiothreitol, 0.5 mM ATP, and 100 μg/ml bovine serum albumin, and $4 \times 10^5$ Units/ml T4 DNA ligase at 5° C. for 15 hours.

Calcium-shocked E. coli strain SK2267 ($F^-$, $gal^-$, $thi^-$, $T_1^R$, hsdR4, $recA^-$, $endA^-$, sbcB15) cells (0.2 ml), prepared as described by R. W. Davis, et al., "Advances Bacterial Genetics" Cold Spring Harbor Laboratory, N.Y. (1980) were transformed with the ligation mixture containing 0.2 μg linearized pGX251 and 0.4 μg of the 2.15 kb Eco RV fragment. Colonies were selected on standard L-broth plates containing 50 μg/ml ampicillin. An ampicillin resistant transformant designated strain GX3311 produced approximately 1 μg/$A_{600}$ unit of Protein A, determined by the method of Lofdahl, et al. (supra). The plasmid carried by this strain, designated pgX2901, consisted of a single copy of the 2.15 kb Eco RV fragment in pGX251.

EXAMPLE III

B. subtilis competent cell transformation by pGX251 containing Protein A gene and Protein A production therewith Competent cells of B. subtilis, strain BR151 (Lovett, P. S., et al., J. Bacteriol., 127, 817–828 (1976)) were transformed with 0.3 μg/ml plasmid pGX251 containing the protein A gene. To prepare competent cells, B. subtilis strain BR151 was grown overnight at 37° C. on tryptose blood agar base (Difco). Cells were resuspended in 10 ml SPI medium supplemented with 50 μg/ml each of lysine, tryptophan, and methionine to give a reading of 50–70 on a Klett-Summerson colorimeter equipped with a green filter (Klett Mfg. Co., New York). SPI medium consists of 1.4% $K_2HPO_4$, 0.6% $KH_2PO_4$, 0.2% $(NH_4)_2SO_4$, 0.1% sodium citrate·$2H_2O$, 0.5% glucose, 0.1% yeast extract (Difco), 0.02% Bacto-Cusamino acids (Difco), and 0.02% $MgSO_4·7H_2O$. The cultures were incubated at 37° on a rotary shaker (200–250 rpm) for 3–4½ hours until logarithmic growth ceased and the cells entered early stationary phase. The cells were then diluted 10 fold into the same medium supplemented with 0.5 mM $CaCl_2$. Incubation was continued for 90 min. The cells were then centrifuged for 5 min. at room temperature, and resuspended in 1/10 volume of spent medium. 1 ml aliquots of the cell suspensions were frozen in liquid nitrogen and stored at $-80°$ C. for use.

For transformation, the frozen competent cells were thawed quickly at 37° and diluted with an equal volume of SPII medium supplemented as above with amino acids. SPII is the same as SPI except that the concentration of $MgSO_4$ is increased to 0.04% and 2 mM ethyleneglycol-bis-($\beta$-aminoethylether)-N,N,N',N'-tetraacetic acid (EGTA) is added. Cells (0.5 ml) are mixed with 0.1 to 5 μg of DNA in $13 \times 100$ mm glass tubes. The cell suspensions are rotated at 37° C. for 30 min. Penassay broth (Difco) (1–2 ml) is then added and incubation continued for 60 min. at 37° C. Cells are then recovered by centrifugation, resuspended in 0–2 ml Penassay broth, and plated on LB agar plates containing 5–10 μg/ml chloramphenicol.

Successful transformants were selected at 5 μg/ml chloramphenicol. The transformed B. subtilis strain was designated GX3308. This strain was shown to produce small quantitites of Protein A by the procedure of Lofdahl, et al. (supra), but lost the plasmid quickly upon culturing in a nutrient medium.

EXAMPLE IV

Insertion of 1 copy of the 2.15 kb fragment into Plasmid pGX284

Plasmid pGX284 (containing an E. coli replicon derived from plasmid pBR322, the gene for ampicillin resistance, the gene for chloramphenicol resistance, a unique EcoRV site, and an undetermined *B. subtilis* chromosomal sequence) was linearized by endonuclease digestion with EcoRV at a concentration of 40 μg/ml in EcoRV buffer for 1 hour at 37° C. Digestion was terminated by incubation for 8 minutes at 65° C. and was determined to be complete by agarose gel electrophoresis. The 2.15 kb EcoRV fragment from Example I and linearized pGX284 were ligated at a concentratin of 200 μg/ml EcoRV fragment, 100 μg/ml linearized pGX284 under the conditions described in Example II.

Calcium-shocked *E. coli* strain SK2267 cells were transformed with the ligation mixture containing 0.2 μg linearized pGX284 and 0.4 μg 2.15 kb EcoRV fragment. Colonies were isolated on standard L-broth plates containing 50 μg/ml ampicillin. An ampicillin resistant transformant designated strain GX3320 produced approximately 1 μg/$A_{600}$ unit of Protein A. The plasmid carried by this strain, designated pGX2907 was determined to consist of a single copy of the 2.15 kb EcoRV fragment inserted into pGX284. Transformed Strain GX3320 has been deposited with the American Type Culture Collection, Rockville, Md., USA and has been designated ATCC No. 39344.

EXAMPLE V

*B. subtilis* protoplast transformation by pGX284 containing single copy of Protein A gene and production of Protein A therewith Protoplasts derived from *B. subtilis* strain 1S53 (spo-0AΔ677) were transformed with 0.1 μg/ml plasmid pGX2907 containing a single copy of the Protein A gene. Strain 1S53 was obtained from the Bacillus Genetic Stock Center, Ohio State University, Dept. of Microbiology, 484 West 12th Ave., Columbus, Ohio 43210 USA. Successful transformants were selected at 5 μg/ml chloramphenicol. A transformant (designated strain GX3305) was found to produce approximately 50 μg/ml Protein A in the extracellular growth medium when grown in a medium containing (per liter) 33 g tryptone, 20 g Yeast extract, 7.4 g NaCl, 12 ml 3M NaOH, 8 g $Na_2HPO_4$, 4 g $KH_2PO_4$ for 17 hours at 37° C. GX3305 has been deposited with the American Type Culture Collection, Rockville, Md., U.S.A. and has been designated ATCC No. 39345.

EXAMPLE VI

Insertion of 2 tandem copies of the 2.15 kb fragment into Plasmid pGX284

From the same tranformation described in Example IV, an ampicillin resistant transformant was isolated (designated strain GX3202-2) which was determined by restriction endonuclease digest anlaysis to carry a plasmid (designated pGX2907-2) in which two tandem copies of the 2.15 kb EcoRV fragment had been inserted into pGX284.

EXAMPLE VII

*B. subtilis* transformation by pGX284 containing two tandem copies of Protein A gene and production of Protein A therewith Competent cells of *B. subtilis* strain BR151 were transformed with 0.3 μg/ml plasmid pGX2907-2, containing two tandem copies of the Protein A gene. Successful transformants were selected at 10 μg/ml chloramphenicol. One transformant designated strain GX3302-2 was grown in a standard fermenter (8L) containing 2×L Broth for 7 hours. The final yield of Protein A was 47 mg/l in the extracellular growth medium as determined by IgG binding activity by a competitive ELISA procedure as described by Lofdahl et al. (supra).

What is claimed is:

1. A plasmid vector comprising a DNA sequence specifying Protein A; expression signals operably linked to said DNA sequence for directing expression of the Protein A DNA sequence in a Gram-positive microorganism of the species "*B. subtilis*"; a selectable phenotypic marker which is expressable in a Gram-positive microorganism of the species "*B. subtilis*"; and a region of sequence homology with a chromosome of a Gram-positive microorganism of the species "*B. substilis*", said region of sequence homology being capable of permitting integration of the Protein A DNA sequence into said chromosome.

2. The plasmid vector of claim 1 further comprising a selectable phenotypic marker which is expressable in *E. coli* and a functional *E. coli* replicon.

3. A method of producing Protein A comprising cultivating in a nutrient medium a transformed Gram-positive microorganism of the species "*B. subtilis*" transformed by a vector containing a nucleotide sequence coding for Protein A and expression signals operably linked to said DNA sequence for directing expression of Protein A in the transformed microorganism, to produce protein A; wherein the vector contains a DNA fragment homologous to a region of the chromosome of said microorganism, and the nucleotide sequence coding for Protein A is integrated into the microorganism host chromosome under recombination conditions.

4. The method of claim 3 wherein the vector is a plasmid capable of replication in *E. coli*.

5. The method of claim 4 wherein plasmids are prepared which contain DNA fragments homologous to different regions of the chromosome of the Gram-positive microorganism, and such plasmids are linearly integrated into their respective homologous regions of the host chromosome under recombination conditions resulting in multiple insertions into the host chromosome.

6. The method of claim 4 wherein the plasmid contains a DNA fragment homologous to sequences of the chromosomes of more than one species of Gram-positive bacteria.

7. The method of claim 4 wherein the plasmid contains more than one copy of the nucleotide sequence coding for Protein A.

8. The method of claim 4 wherein the plasmid contains more than one copy of the nucleotide sequence coding for Protein A.

9. The method of claim 4 wherein the plasmid contains two tandem copies of the nucleotide sequence coding for Protein A.

10. A protein A-producing strain of a Gram-positive microorganism of the species "*B. subtilis*", wherein the chromosome of said microorganism comprises a heterologous Protein A gene under the requesting central of expression signals capable of directing expression of the Protein A gene.

11. A method of producing Protein A comprising cultivating in a nutrient medium a strain of *Bacillus subtilis*, having the identifying characteristics of strain GX3305 (ATCC No. 39345).

12. *Bacillus subtilis* strain GX3305 (ATCC No. 39345).

* * * * *